(12) United States Patent
Metzler et al.

(10) Patent No.: US 7,617,006 B2
(45) Date of Patent: *Nov. 10, 2009

(54) MEDICAL ELECTRICAL LEAD FOR SPINAL CORD STIMULATION

(75) Inventors: Michael E. Metzler, Eden Prairie, MN (US); Jessica L. Tower, Minneapolis, MN (US); Mary L. Boatwright, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 350 days.

This patent is subject to a terminal disclaimer.

(21) Appl. No.: 11/413,582

(22) Filed: Apr. 28, 2006

(65) Prior Publication Data

US 2007/0255373 A1 Nov. 1, 2007

(51) Int. Cl.
*A61N 1/05* (2006.01)

(52) U.S. Cl. .................................................... 607/117

(58) Field of Classification Search ............... 607/117, 607/118, 152; 600/393
See application file for complete search history.

(56) References Cited

U.S. PATENT DOCUMENTS

| | | | |
|---|---|---|---|
| 3,654,933 A | 4/1972 | Hagfors | |
| 3,724,467 A | 4/1973 | Avery et al. | |
| 3,738,368 A | 6/1973 | Avery et al. | |
| 3,774,618 A | 11/1973 | Avery | |
| 4,044,774 A | 8/1977 | Corbin et al. | |
| 4,573,481 A | 3/1986 | Bullara | |
| 4,940,065 A | 7/1990 | Tanagho et al. | |
| 5,000,194 A * | 3/1991 | van den Honert et al. | 607/137 |
| 5,417,719 A | 5/1995 | Hull et al. | |
| 5,643,330 A | 7/1997 | Holsheimer et al. | |
| 6,066,165 A | 5/2000 | Racz | |
| 6,205,361 B1 | 3/2001 | Kuzma et al. | |
| 6,308,103 B1 | 10/2001 | Gielen | |
| 6,319,241 B1 | 11/2001 | King et al. | |
| 6,587,733 B1 | 7/2003 | Cross, Jr. et al. | |
| 6,999,820 B2 | 2/2006 | Jordan | |
| 2002/0111661 A1* | 8/2002 | Cross et al. | 607/117 |
| 2003/0204228 A1* | 10/2003 | Cross et al. | 607/116 |
| 2003/0229387 A1 | 12/2003 | Cross, Jr. et al. | |
| 2004/0243205 A1 | 12/2004 | Keravel et al. | |
| 2004/0243208 A1 | 12/2004 | Jordan | |
| 2005/0004639 A1 | 1/2005 | Erickson | |
| 2005/0075707 A1 | 4/2005 | Meadows et al. | |
| 2005/0203600 A1 | 9/2005 | Wallace | |
| 2007/0027514 A1* | 2/2007 | Gerber | 607/116 |
| 2007/0150036 A1* | 6/2007 | Anderson | 607/116 |
| 2007/0179579 A1* | 8/2007 | Feler et al. | 607/117 |

FOREIGN PATENT DOCUMENTS

WO 99/56818 11/1999

* cited by examiner

*Primary Examiner*—Kennedy J Schaetzle
(74) *Attorney, Agent, or Firm*—Fredrikson & Byron, P.A.

(57) ABSTRACT

A medical electrical lead for spinal cord stimulation includes a first column of electrode surfaces and a second column of electrode surfaces, both coupled to a distal portion of the lead such that the two columns extend alongside one another and are spaced apart from one another. Each electrode surface of the first column is coupled to a corresponding conductor of a first plurality of conductors of a first lead body, and each electrode surface of the second column is coupled to a corresponding conductor of a second plurality of conductors of a second lead body. The first and second lead bodies are coupled together by the distal portion of the lead, and each electrode surface extends laterally away from the respective lead body.

15 Claims, 5 Drawing Sheets

MEDICAL ELECTRICAL LEAD FOR SPINAL CORD STIMULATION

CROSS-REFERENCE TO RELATED APPLICATION

This application is related to commonly assigned application Ser. No. 11/413,581, being filed on the same date and entitled, NOVEL ASSEMBLY METHOD FOR SPINAL CORD STIMULATION LEAD, which is hereby incorporated by reference in its entirety.

TECHNICAL FIELD

The present invention is related to spinal cord stimulation therapy and more particularly to medical electrical leads for delivering the stimulation therapy.

BACKGROUND

Electrical stimulation of a spinal cord, which induces pain-relieving paresthesia, can be provided by implantable systems that include electrodes coupled to elongate electrical leads. Such electrodes may be percutaneously or surgically introduced into the epidural space surrounding the spinal cord. Medical electrical leads which include an array of electrodes provide flexibility for selection from a variety of stimulation patterns upon implantation without having to physically reposition the lead within the epidural space. Such leads, wherein the electrode array is coupled along a body of the lead or along a distal paddle-like termination of the lead body, are known in the art. However, there is still a need for new spinal cord lead designs including distal ends that fit securely within the epidural space surrounding the spinal cord, and conform to the spinal cord so that an array or plurality of electrodes coupled to the distal end are in intimate contact with the dura mater enclosing the spinal cord.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides practical illustrations for implementing exemplary embodiments of the present invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized.

Figure 1B:
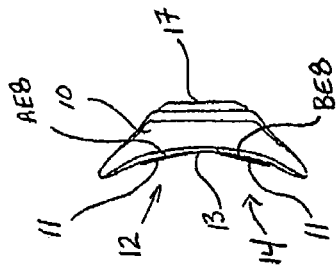
FIG. 1B is an end view of the lead shown in FIG. 1A.
Figure 1A:
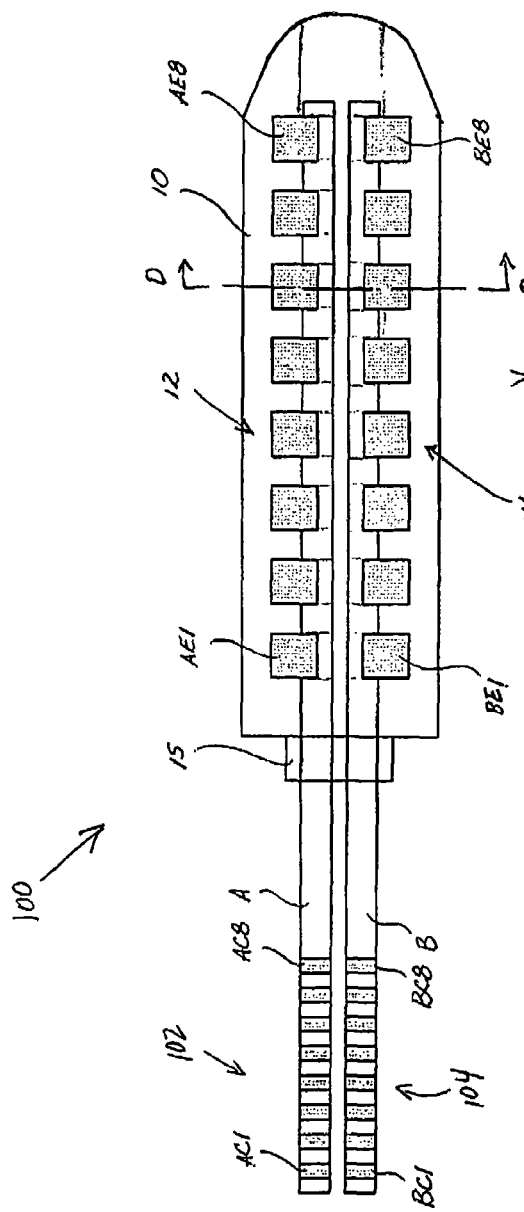
FIG. 1A is a plan view of a medical electrical lead, according to some embodiments of the present invention.

FIG. 1A is a plan view of a medical electrical lead 100, according to some embodiments of the present invention. FIG. 1A illustrates lead 100 including a first column 12 of electrodes AE1-AE8 and a second column 14 of electrodes BE1-BE8 coupled to an insulative distal portion 10, which may be formed from silicone rubber; a first lead body A and a second lead body B each extend proximally from distal portion 10 to corresponding connectors 102 and 104. According to the illustrated embodiment, each lead body A, B includes a plurality of insulated conductors; each conductor of each of the pluralities of conductors couples a corresponding electrode of electrodes AE1-AE8 and BE1-BE8 to a corresponding connector contact of contacts AC1-AC8 and BC1-BC8, according to methods known to those skilled in the art, which will be described in greater detail below. Those skilled in the art will appreciate that connectors 102 and 104 may either be connected directly to a stimulation device or to an extension, or adaptor, which includes one or two connectors for connection with the stimulation device. FIG. 1A further illustrates a strain relief 15 extending proximally from distal portion 10 over lead bodies A, B.

Figure 1C:
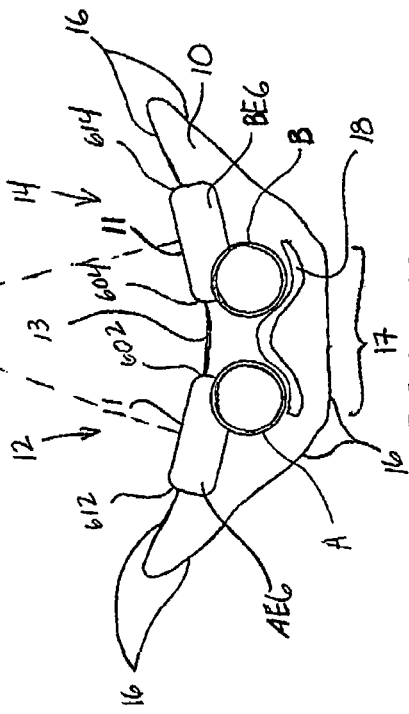
FIG. 1C is a section view, through section line D-D of FIG. 1A.

FIG. 1B is an end view of lead 100; and FIG. 1C is a section view through section line D-D of FIG. 1A. FIGS. 1B-C illustrate each of electrodes AE1-AE8 of first column 12 and each of electrodes BE1-BE8 of second column 14 including an approximately planar electrode surface 11; each electrode surface 11 of first column 12 is angled toward each electrode surface 11 of second column 14, such that planes (represented by dashed lines in FIG. 1C), which extend along and approximately orthogonally out from each column 12, 14 intersect one another. According to an exemplary embodiment of the present invention, a surface area of each electrode surface 11 is approximately six square millimeters, a longitudinal spacing between each electrode AE1-AE8 and BE1-BE8, within each column 12, 14 is approximately four millimeters, edge-to-edge, and approximately seven millimeters, center-to-center, and a spacing between columns 12 and 14 is between approximately three and four millimeters, center-to-center, and between approximately one and two millimeters, edge-to-edge. Although FIG. 1A illustrates each electrode surface 11 of first column 12 longitudinally aligned with the corresponding electrode surface 11 of second column 14, the scope of the present invention is not so limited, and alternate embodiments may include staggered columns of electrode surfaces. Furthermore, alternate embodiments of the present invention can include electrode surfaces having a convex curvature rather than being approximately planar, as illustrated.

Figure 2B:
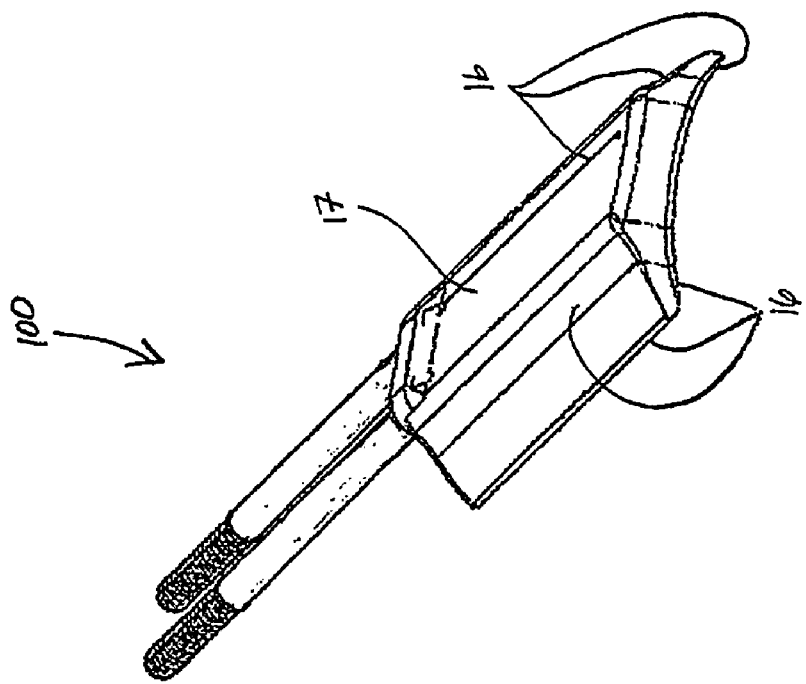
FIGS. 2A-B are a perspective views of the lead shown in FIG. 1A.
Figure 2A:
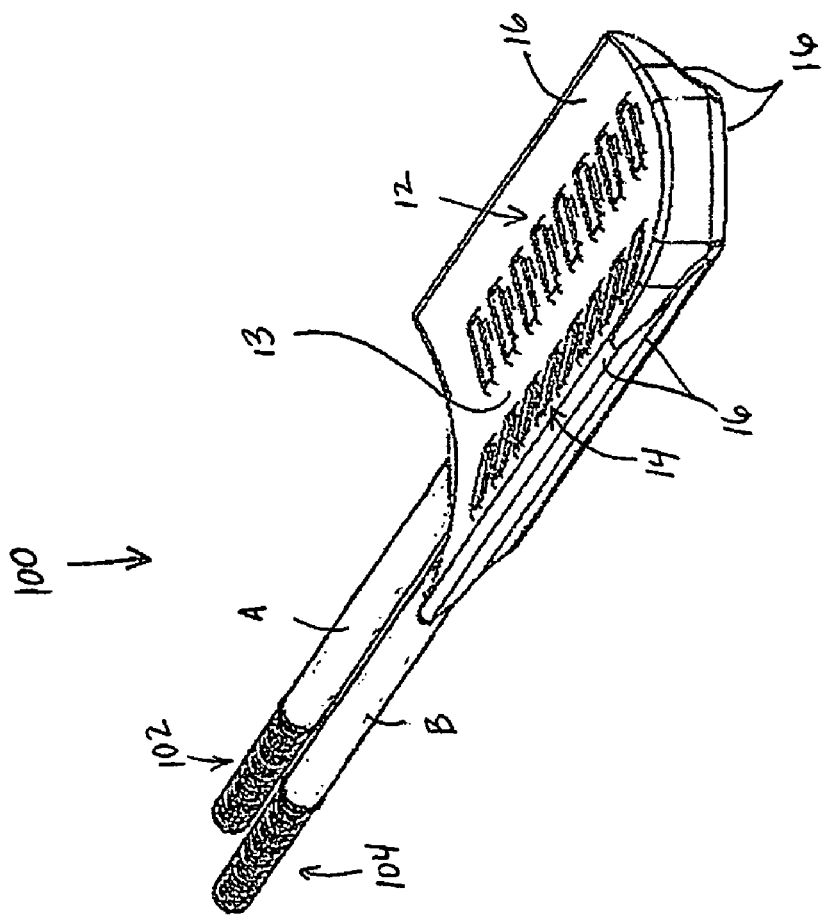

FIGS. 1B-C further illustrate distal portion 10 including a first surface 13 extending between an inner edge 602 of each electrode surface 11 of first column 12 and an inner edge 604 of each electrode surface 11 of second column 14, and a second surface 16 extending from an outer edge 612 of each electrode surface 11 of first column 12 to an outer edge 614 of each electrode surface 11 of second column 14. According to the illustrated embodiment, first surface 13 curves in a concave fashion and second surface 16 extends behind first and second columns 12, 14 and includes an approximately flat portion 17 disposed opposite first and second columns 12, 14. FIGS. 2A-B are perspective views of lead 100, which further illustrate first surface 13 and flat portion 17 of second surface 16. According to an exemplary embodiment, distal portion has a length between approximately sixty millimeters and approximately seventy millimeters, a width between approximately eight and approximately twelve millimeters, and a thickness, defined from flat portion 17 of surface 16 across to first surface 13, of approximately two millimeters; and, surface 13 has a radius of curvature of approximately nine millimeters.

FIG. 1C further illustrates electrodes AE6 and BE6, representative of each electrode of columns 12 and 14, respectively, extending, in a cantilever fashion, laterally away from respective lead bodies A, B, which extend into distal portion 10. Each electrode AE1-AE8 and BE1-BE6 may be coupled, as such, for example, by laser welding, directly to the respective conductor within the corresponding lead body A, B, or to a conductive ring, which is coupled to the respective conductor and disposed about the corresponding lead body A, B. According to the illustrated embodiment, surface 11 of each electrode AE1-AE8 and BE1-BE6 protrudes slightly from adjacent portions of surfaces 13, 16, but, according to alternate embodiments, electrode surfaces 11 are flush with adjacent portions of surfaces 13, 16.

Figure 3B:
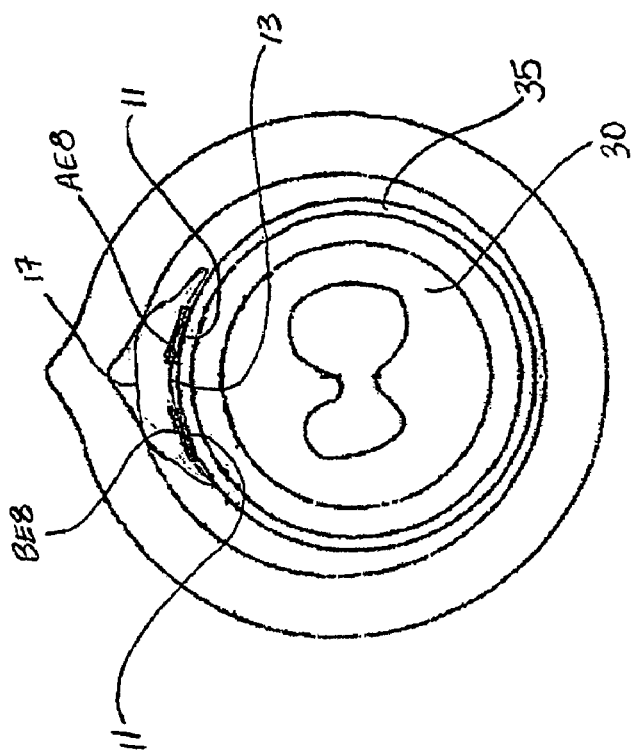
FIG. 3B is an end view of the implanted lead shown in FIG. 3A.
Figure 3A:
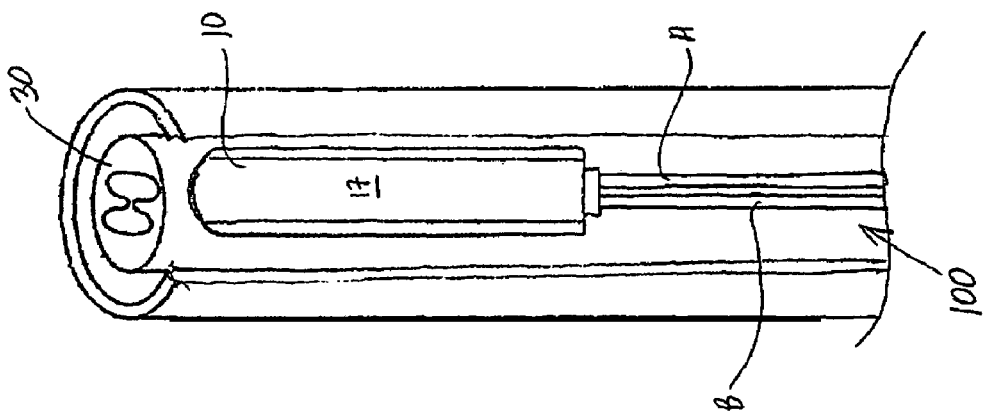
FIG. 3A is a schematic including a portion of the spinal canal cut away so that the lead of FIG. 1A may be seen implanted in the epidural space surrounding a spinal cord.

FIG. 3A is a schematic including a portion of the spinal canal cut away so that lead 100 may be seen implanted in the epidural space of a spinal cord 30; and FIG. 3B is an end view of the implanted lead 100. FIGS. 3A-B illustrate distal portion 10 of lead implanted in the epidural space such that electrode surfaces 11 are in intimate contact with the dura mater 35 surrounding spinal cord 30. Methods for implanting surgical spinal cord leads, such as lead 100, are well known to those skilled in the art. With reference to FIGS. 3A-B, it may be appreciated that the pre-formed profile of distal portion 10, along with the angled arrangement of electrode surfaces 11, as described in conjunction with FIG. 1C, may greatly enhance the conformance of distal portion 10 about spinal cord 30 such that electrodes 11 contact the dura mater 35, as shown, for relatively efficient stimulation of spinal cord 30. Furthermore, the preformed shape of distal portion 10 facilitates the fit of distal portion 10 within the epidural space.

Figure 4:
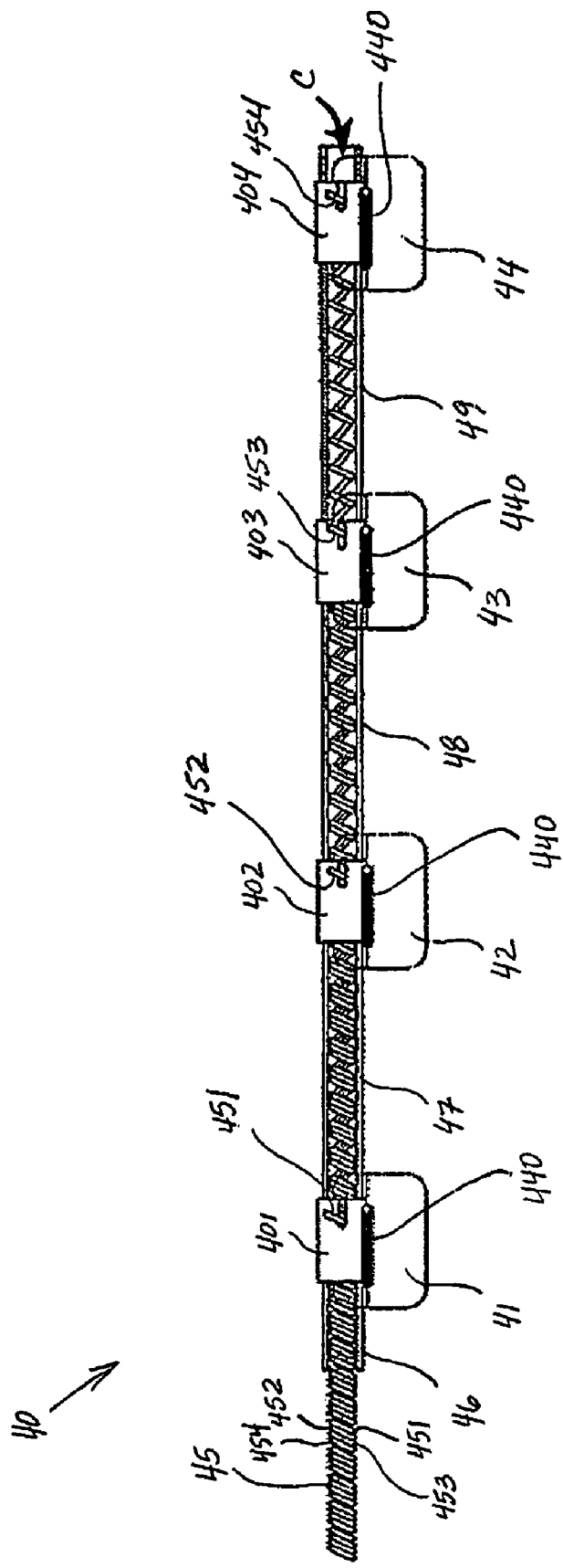
FIG. 4 is a plan view including a partial section of a portion of a lead body assembly, according to some embodiments of the present invention.

FIG. 4 is a plan view including a partial section of a portion of a lead body assembly 40, according to some embodiments of the present invention. FIG. 4 illustrates assembly 40 including four conductors 451-454 wound in a coil 45 and each conductor 451-454 coupled to a conductive ring 401-404, respectively, which is, in turn, coupled to an electrode 41-44, respectively. Conductors 451-454 are isolated from one another by an overlay of insulation material surrounding each of conductors 451-454, examples of which include, but are not limited to, polyimide, polytetrafluoroethylene (PTFE), and ethylene tetrafluoroethylene (ETFE). According to the illustrated embodiment, a distal end of each conductor 451-454 is hooked in a slot of the corresponding conductive ring 401-404, and laser welded thereto, and each electrode 41-44, whose active electrode surface is shown facing into the page, is coupled to the corresponding ring 401-404 via a laser weld, for example, as illustrated along line 440. Those skilled in the art will appreciate that conductor 45 extends proximally to a connector, for example, similar to connectors 102 and 104 of FIG. 1A, where each conductor 451-454 is coupled to a corresponding connector contact, for example, in manner similar to that described for rings 401-404. Although FIG. 4 illustrates assembly 40 including only four conductors and electrodes, it should be understood that lead body A or lead body B, of FIG. 1A, which each include eight conductors and electrodes, may incorporate an assembly constructed in a similar manner to that of assembly 40, but including four additional conductors, rings and electrodes.

According to certain methods of the present invention, a step of coupling electrodes to rings, for example, as illustrated in FIG. 4, is performed prior to coupling two of lead body assemblies 40 together. According to some embodiments of the present invention, conductive rings 401-404 may form electrode surfaces of completed lead assemblies that include assembly 40, and have been originally manufactured for independent use, for example, as percutaneous spinal cord stimulation leads. However, alternate embodiments of the present invention need not include conductive rings, such as rings 401-404, and each electrode, for example, electrodes 41-44, may be coupled directly to a corresponding conductor, for example, conductors 452-453.

FIG. 4 further illustrates insulation members 46, 47, 48 and 49 each extending around a portion of coil 45. According to some methods of the present invention, after electrodes 41-44 are coupled to rings 401-404, an adhesive, for example, silicone medical adhesive, is injected, per arrow C, to fill lumens of members 46, 47, 48 and 49, prior to coupling a two of assemblies 40 together.

Figure 5A:
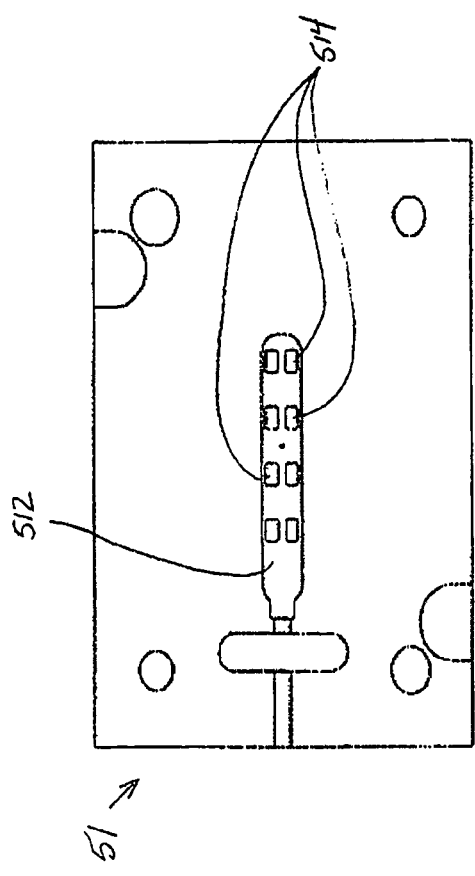
FIGS. 5A-B are plan views of mating mold halves, which may be used to couple lead bodies, according to some methods of the present invention.
Figure 5B:
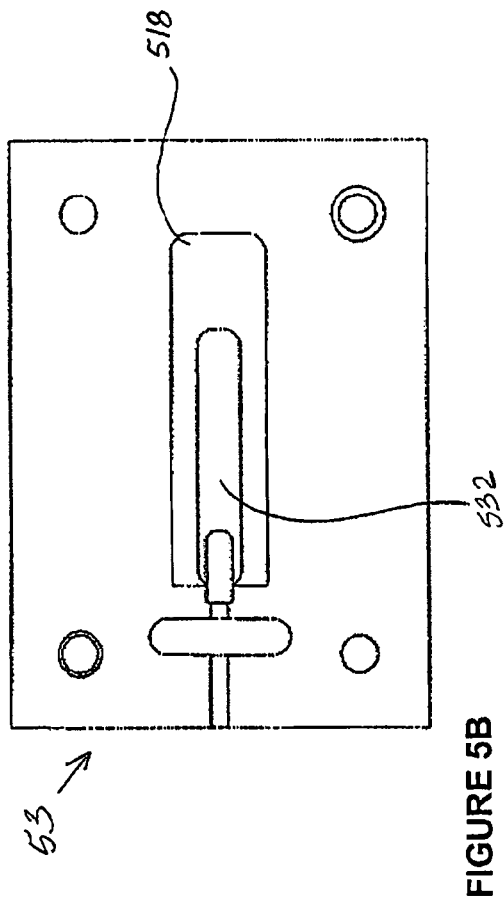

Coupling two of assemblies 40 together may be accomplished by forming a paddle-like insulative member around the pair assemblies 40 either by a transfer or an insert molding method, known to those skilled in the art; the paddle-like member, according to some embodiments is similar to distal portion 10 described in conjunction with FIGS. 1A-2B. FIGS. 5A-B are plan views of mating mold halves 51, 53, which may be used to couple lead bodies, via a transfer molding method, after electrodes 41-44 have been coupled to conductors 451-454. FIG. 5A illustrates first mold half 51 including a cavity 512 for forming, in conjunction with a cavity 532 of mating mold half 53 shown in FIG. 5B, a paddle-like insulative distal portion, for example, distal portion 10 illustrated in FIGS. 1A-2B.

FIG. 5A further illustrates electrode reliefs 514 disposed at locations in cavity 512 to correspond with positions of electrode surfaces of electrodes 41-44 of each of two assemblies 40 that will be placed between mold halves 51, 53. Reliefs 514 prevent the flow of injected material, for example, MDX silicone rubber, which forms the paddle-like member, into sites corresponding to electrode surfaces of electrodes 41-44, so that the electrode surfaces will not be covered with the insulative material.

FIG. 5B further illustrates mold half 53 including a relief 518 for placement of a sheet of mesh material, which will be embedded within the paddle-like member, for example, as illustrated in FIG. 1C where the mesh is denoted by item number 18. Mesh 18 may enhance the structural integrity of the coupling of lead bodies A and B by distal portion 10. After the molding process is completed, excess mesh material may be trimmed away about the perimeter of the paddle-like member.

Referring back to FIGS. 1A-2B, it may be appreciated that a profile of cavity 512, in between reliefs 514, may have a convex curvature, for example, to form surface 13, and a profile of cavity 513 may include a flat portion, for example, to form surface 17. It should be noted that, although a transfer molding process calls for the injection of the material into mating cavities 512, 513 prior to insertion of assemblies 40 between mold halves 51, 53, other types of molding processes, which are within the scope of the present invention, for example, insert molding, call for insertion of assemblies 40 into a mold, prior to the injection of the material.

In the foregoing detailed description, the invention has been described with reference to specific embodiments. However, it may be appreciated that various modifications and changes can be made without departing from the scope of the invention as set forth in the appended claims.

The invention claimed is:

1. A medical electrical lead for spinal cord stimulation, comprising:

a first elongate lead body including a first plurality of conductors isolated from one another and a first plurality of conductive rings longitudinally spaced apart from one another and separated from one another by a first set of insulating members, each conductive ring of the first plurality of conductive rings being electrically coupled to a corresponding conductor of the first plurality of conductors;

a second elongate lead body including a second plurality of conductors isolated from one another and a second plurality of conductive rings longitudinally spaced apart from one another and separated from one another by a first set of insulating members, each conductive ring of the second plurality of conductive rings being electrically coupled to a corresponding conductor of the second plurality of conductors;

a distal portion surrounding the first and second plurality of conductive rings and coupling the first lead body to the second lead body, the first and second lead bodies extending proximally from the distal portion;

a first column of electrode surfaces being exposed along the distal portion, each of the electrode surfaces of the first column being electrically coupled to a corresponding conductor of the first plurality of conductors, via a weld to a corresponding conductive ring of the first plurality of conductive rings, and each of the electrode surfaces of the first column extending laterally away from the first lead body; and a second column of electrode surfaces being exposed along the distal portion and extending alongside, and spaced apart from, the first column, each of the electrode surfaces of the second column being electrically coupled to a corresponding conductor of the second plurality of conductors, via a weld to a corresponding conductive ring of the second plurality of conductive rings, and each of the electrode surfaces of the second column extending laterally away from the second lead body.

2. The lead of claim 1, wherein the distal portion includes a concave surface extending from an inner edge of each electrode surface of the first column to an inner edge of each electrode surface of the second column.

3. The lead of claim 1, wherein the distal portion includes a surface extending from an outer edge of each electrode surface of the first column to an outer edge of each electrode surface of the second column, and the surface includes a flat portion disposed opposite the first and second columns of electrode surfaces.

4. The lead of claim 1, wherein each electrode surface of the first column is longitudinally aligned with a corresponding electrode surface of the second column.

5. The lead of claim 1, further comprising a mesh panel extending between the first and second lead bodies within the distal portion.

6. The lead of claim 1, wherein each of the electrode surfaces of the first and second columns are approximately planar.

7. The lead of claim 6, wherein each electrode surface of the first column is angled toward each electrode surface of the second column such that a plane extending along the first column and orthogonally out from the electrode surfaces of the first column intersects a plane extending along the second column and orthogonally out from the electrode surfaces of the second column.

8. The lead of claim 1, further comprising:
a first connector extending proximally from the first lead body and including a first plurality of contact surfaces, each contact surface being electrically coupled to a corresponding conductor of the first plurality of conductors; and
a second connector extending proximally from the second lead body and including a second plurality of contact surfaces, each contact surface being electrically coupled to corresponding conductor of the second plurality of conductors.

9. The lead of claim 1, wherein each of the first and second lead bodies is formed by a medical electrical lead of a type having a generally cylindrical configuration adapted for percutaneous implantation.

10. A medical electrical lead for spinal cord stimulation, comprising:
first and second columns of electrode surfaces, each electrode surface being approximately planar;
a first elongate lead body including a first plurality of conductors isolated from one another and a distal portion to which the first column of electrode surfaces is coupled, each electrode surface of the first column being electrically coupled to a corresponding conductor of the first plurality of conductors;
a second elongate lead body including a second plurality of conductors isolated from one another and a distal portion to which the second column of electrode surfaces is coupled, each electrode surface of the second column being electrically coupled to a corresponding conductor of the second plurality of conductors; and
a paddle-like member coupling together the distal portions of the first and second elongate lead bodies, the paddle-like member including a first side along which each electrode surface of the first and second columns is exposed;
wherein each electrode surface of the first and second columns extend laterally away from the distal portion of the first and second elongate lead bodies, respectively; and
each electrode surface of the first column is angled toward each electrode surface of the second column such that a plane extending along the first column and orthogonally out from the electrode surfaces of the first column intersects a plane extending along the second column and orthogonally out from the electrode surfaces of the second column.

11. The lead of claim 10, wherein the paddle-like member further includes a second side opposite the first side thereof, the second side including an approximately flat surface extending between the first and second columns of electrode surfaces.

12. The lead of claim 10, wherein each electrode surface of the first column is longitudinally aligned with a corresponding electrode surface of the second column.

13. The lead of claim 10, further comprising a mesh panel extending between the distal portions of the first and second lead bodies within the paddle-like member.

14. The lead of claim 10, further comprising:
a first connector extending proximally from the first lead body and including a first plurality of contact surfaces, each contact surface being electrically coupled to a corresponding conductor of the first plurality of conductors; and
a second connector extending proximally from the second lead body and including a second plurality of contact surfaces, each contact surface being electrically coupled to a corresponding conductor of the second plurality of conductors.

15. The lead of claim 10, wherein each of the first and second lead bodies is formed by a medical electrical lead of a type having a generally cylindrical configuration adapted for percutaneous implantation.

* * * * *